US008034302B1

(12) United States Patent
Alcantar et al.

(10) Patent No.: US 8,034,302 B1
(45) Date of Patent: Oct. 11, 2011

(54) TRANSPARENT CONDUCTING COMPOSITES (TTCS) FOR CREATING CHEMICALLY ACTIVE SURFACES

(75) Inventors: Norma A Alcantar, Tampa, FL (US); Julie Harmon, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 12/711,637

(22) Filed: Feb. 24, 2010

Related U.S. Application Data

(60) Provisional application No. 61/154,809, filed on Feb. 24, 2009.

(51) Int. Cl.
*G01N 33/22* (2006.01)
(52) U.S. Cl. .......................... 422/420; 436/106; 436/524
(58) Field of Classification Search .................... 422/57, 422/420; 436/106, 524
See application file for complete search history.

(56) References Cited

OTHER PUBLICATIONS

Pichot et al., Flexible Solid-State Photoelectrochromic Windows, Journal of The Electromechanical Society, 1999, vol. 146, No. 11, pp. 4324-4326.
Ho et al., Power Effects in Indium-Zinc Oxide Thin Films for OLEDs on Flexible Applications, Journal of The Electromechanical Society, 2005, vol. 152, No. 1, pp. G57-G61.
Chopra et al., Thin-Film Solar Cells: An Overview, Prog. Photovolt.: Res. Appl., 2004, vol. 12, pp. 69-92.
Woods et al., Wide-Bandgap CIAS Thin-Film Photovoltaics with Transparent Back Contacts for Next Generation Single Multi-Junction Devices, Materials Science and Engineering B, 2005, vol. 116, pp. 297-302.
Marnellos et al., Catalytic Studies in Electromechanical Membrane Reactors, Solid State Ionics, 2004, vol. 175, pp. 597-603.
Rosch et al., Electrochemical Characterization of Ni-Ce0.9Gd0.1O2-Alpha for SOFC Anodes, Solid State Ionics, 2004, pp. 113-117.
Liu et al., Cutting and Wearing Characteristics of TiC-Based Cermets Cutters with Nano-TiN Addition, Journal of Materials Processing Technology, 2005, vol. 161, pp. 478-484.
Kee et al., Solid-Oxide Fuel Cells with Hydrocarbon Fuels, Proceedings of the Combustion Institute, 2005, vol. 30, pp. 2379-2404.
Kim et al., Cu-Ni Cermet Anodes for Direct Oxidation of Methane in Solid-Oxide Fuel Cells, Journal of The Electrochemical Society, 2002, vol. 149, No. 3, pp. A247-A250.
Baldus et al., Writing Conducting Lines Into Alumina Ceramics by a Laser Dispersing Process, Journal of the European Ceramic Society, 2004, vol. 24, pp. 3759-3767.
Chen et al., Comparison Study of ITO Thin Films Deposited Onto Different Substrates at Room Temperature, Journal of Materials Science Letters, 2000, vol. 19, pp. 99-101.
Singh et al., Solid Oxide Fuel Cells: Technology Status, International Journal of Applied Ceramic Technology, 2004, vol. 1, No. 1, pp. 5-15.

(Continued)

*Primary Examiner* — Jill Warden
*Assistant Examiner* — Monique Cole
(74) *Attorney, Agent, or Firm* — Robert Varkonyi Smith & Hopen, P.A.

(57) ABSTRACT

Disclosed are chemically active surfaces for the detection of nitroaromatic, nitramine, and nitrate ester compounds, the primary constituents of explosive devices. Transparent conductive composites (TCCs) combine with gold nanoparticles in a conducting polymer matrix to create a conductive, flexible, and electrochromic material. Hybrid, nanostructured surfaces constructed from TCCs are decorated with conjugated conductive oligomer wires. Selective binding of the target to the oligomer alters the electron charge mobility in the TCC, affecting the redox state. The binding event is identified by measuring the conductivity of the TCC and/or through color changes of the TCC. Conjugated oligomers that are functionalized with thiol groups at one end and nitro-derivative receptors at the other provide the bases for selectivity and sensing. The thiol group anchors the oligomer to the metal sites on the TCC surface and the receptor starts the charge transfer mechanism when targeted with the appropriate molecule.

11 Claims, 9 Drawing Sheets

OTHER PUBLICATIONS

Kumar et al., Conducting Polymers: Emerging Commercial Materials, Defence Science Journal, 1996, vol. 46, No. 2, pp. 91-104.

Takagi, Development and Application of High Strength Ternary Boride Base Cermets, Journal of Solid State Chemistry, 2006, vol. 179, pp. 2809-2818.

Yu et al., Effect of Mo/B Atomic Ratio on the Microstructure and Mechanical Properties of Mo2FeB2 Based Cermets, Int. Journal of Refractory Metals & Hard Materials, 2010, vol. 28, pp. 338-342.

Liu et al., Shape-Adaptable Water-Soluble Conjugated Polymers, J. Am. Chem. Soc., 2003, vol. 125, pp. 13306-13307.

Hoven et al., Electron Injection into Organic Semiconductor Devices from High Work Function Cathodes, PNAS, 2008, vol. 105, No. 35, pp. 12730-12735.

Gaylord et al., Water-Soluble Conjugated Oligomers: Effect of Chain Length and Aggregation on Photoluminescence-Quenching Efficiencies, J. Am. Chem. Soc., 2001, vol. 123, pp. 6417-6418.

Fan et al., Beyond Superquenching: Hyper-Efficient Energy Transfer from Conjugated Polymers to Gold Nanoparticles, PNAS, 2003, vol. 100, No. 11, pp. 6297-6301.

Seo et al., Electronic Properties at Gold/Conjugated-Polyelectrolyte Interfaces, Advanced Materials, 2009, vol. 21, pp. 1006-1011.

Hong et al., Water-Soluble Oligomer Dimers Based on Paracyclophane: A New Optical Platform for Fluorescent Sensor Applications, J. Am. Chem. Soc., 2002, vol. 124, pp. 11868-11869.

Seferos et al., Alpha, Omega-Bis(Thioacetyl)Oligophenylenevinylene Chromophores from Thioanisol Precursors, J. Org. Chem., 2004, vol. 69, pp. 1110-1119.

Seferos et al., Alpha, Omega-Dithiol Oligo(Phenylene Vinylene)s for the Preparation of High-Quality Pi-Conjugated Self-Assembled Monolayers and Nanoparticle-Functionalized Electrodes, Advanced Functional Materials, 2006, vol. 16, pp. 2387-2392.

TRANSPARENT CONDUCTING COMPOSITES (TTCS) FOR CREATING CHEMICALLY ACTIVE SURFACES

CROSS REFERENCE TO RELATED APPLICATIONS

This application is a Non-Provisional Application of co-pending U.S. Provisional Application No. 61/154,809 filed Feb. 24, 2009; which is incorporated herein by reference.

GOVERNMENT SUPPORT

This invention was made with government support under CBET0808053 awarded by the National Science Foundation. The government has certain rights in the invention.

BACKGROUND OF THE INVENTION

The molecules from IEDs (e.g. nitroaromatic, nitramine, and nitrate ester compounds) easily blend with other contaminants in the ambient, decompose rapidly producing various ionized species, and have relatively low vapor pressures compared to other compounds. Consequently, IED compounds (nitroamine, nitroaromatic, and nitrate ester compounds) are hard to detect with precision. Most of the platforms to detect explosive compounds successfully are gas chromatography (GC), ion mobility spectrometry (IMS), and mass spectrometry (MS) within the most frequently used analytical methods. However, the integration of such analytical techniques in the processing of thin film technologies for detecting IED compounds is still under development.

The "electronic nose" concept has also been widely used to investigate new technologies for sensing organic compounds. Most of those technologies have been developed to induce both flexibility and conductivity, and even though there have been important breakthroughs in the field of conducting/flexible films, many challenges such as film transparency and high sensitivity and selectivity are still to be overcome.

New strategies are needed to develop composites that combine conductive components that are embedded in translucid matrices. The challenges are to use the lowest amount of metallic filler without compromising conductivity and develop processing techniques that render adaptability and lower production costs. Despite the tremendous market potential for such films, we lack the fundamental understanding as to how to combine and process such materials to optimize desirable properties, such as flexibility, robustness, and transparency as well as specificity and rate of detection.

SUMMARY OF INVENTION

The invention addresses, inter alia, the need to engineer active surfaces for the detection of nitroaromatic, nitramine, and nitrate ester compounds, which are the primary constituents of explosive devices. Therefore the invention includes, in an illustrative embodiment, TCCs combine with gold nanoparticles in a conducting polymer matrix to create a hybrid material that is conductive, flexible, and electrochromic. Hybrid, nanostructured surfaces constructed from transparent conductive composites (TCCs) are decorated with conjugated conductive oligomer wires. Selective binding of the target to the oligomer alters the electron charge mobility in the TCC, which in turn affects the redox state of the TCC. The binding event, therefore, can be effectively identified by measuring the conductivity of the TCC and/or through color changes of the TCC. For instance, the TCC can switch from opaque to dark green depending on its redox state. Conjugated oligomers that are functionalized with thiol groups at one end and nitro-derivative receptors at the other provide the bases for selectivity and sensing. The thiol group anchors the oligomer to the metal sites on the TCC surface and the receptor starts the charge transfer mechanism when targeted with the appropriate molecule.

BRIEF DESCRIPTION OF THE DRAWINGS

For a fuller understanding of the invention, reference should be made to the following detailed description, taken in connection with the accompanying drawings, in which:

FIG. 9A is a diagram for the design of an IR-SFA device according to one embodiment of the invention. FIG. 9B is a detail of element A of FIG. 9A showing the decreasing evanescent field and reflected IR radiation from the IR source.

DETAILED DESCRIPTION OF THE PREFERRED EMBODIMENT

The invention includes, in a general embodiment, chemically active surface arrays that can be used, inter alia, to detect the primary constituents of improvised explosive devices (IEDs). The chemically active surfaces are, in a preferred embodiment, comprised of conducting thin films that are both flexible and translucent. Complex materials that exhibit conductivity, flexibility and transparency are preferred for processing the thin films which are capable of "smart responses"

(i.e., surfaces that recognize external stimuli and react by changing their electronic, chemical, mechanical and/or optical properties).

Figure 1:
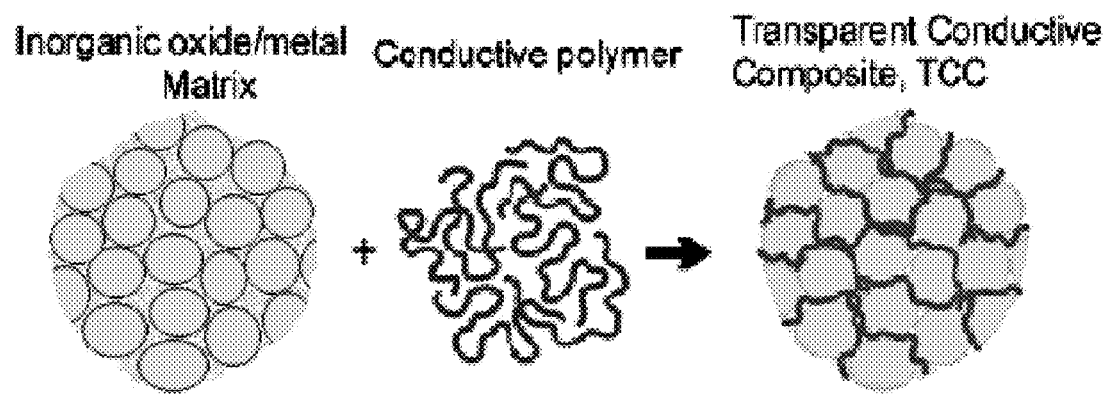
FIG. 1: Schematic of hybrid materials architecture.

In an illustrative embodiment of a device incorporating the novel transparent conductive composites (TCCs), the main compounds of IEDs (e.g. nitroamine, nitroaromatic, and nitrate ester compounds) are detected by arrays of functionalized conjugated conductive oligomer (CCO) wires attached to nanostructured surfaces from the TCCS (FIG. 1). When a nitrate compound specifically binds a CCO, a change in the surface charge alters the redox state of the TCC. As the surface of the TCC is electrochromic, the change inredox state also changes the reflecting visible color of the sensing surface making the films optically responsive. The electrochromic nature of the TCC is created by the combination of translucent and conductive materials. Generally speaking; however, conductive materials such as metals and conductive polymers are not transparent. Therefore, in a preferred embodiment, the invention combines conductive components that are embedded in translucent matrices.

The illustrative embodiment includes a simple but efficient array of active surfaces constructed via microelectronic processing, which avoids false negative or positive signals. This embodiment uses a 3-body system (3BSys) (see FIG. 2) using different functional groups attached to the CCOs. The exposure of one of the surface active bodies containing a generic functional group (i.e., a group that will bind any amine group with a high reaction constant) will provide a background signal. A simple pattern differentiation between two other functional groups of the array results in different resistivity and translucent signals depending on the surface reaction, which in turn determines that an IED compound has unambiguously been recognized. Although this example, discussed in detail below, uses a simple array, more complicated arrays of sensors have been explored by other groups and could be incorporated for use with the invention by one of ordinary skill in the art. Therefore, more complicated arrays are contemplated for use with the current invention.

The inventive chemically active surfaces are constructed by combining conductive, dye-doped polymeric matrices with inorganic particles via diffusely connected metal active points, resulting in a translucent network of molecular wires having electrical and optical characteristics similar to ITO. The chemically active surfaces, however, have better chemical resistance, flexibility, and mechanical properties (FIG. 1).

TCC Design

The TCCs are designed to monitor changes in resistivity similar to sensors used in applications such as electronic noses. The basic sensor design consists of surface conductive polymer complexes, coated with gold nanoparticles (5 to 50 nm). Organic molecules that complex with IED compounds such as nitroaromatics are attached to the gold particles via appended —SH groups that self-assemble on gold. The presence of nitroaromatics is detected via changes in resistivity that occur upon association with the organic molecules appended to the gold.

Figure 3:
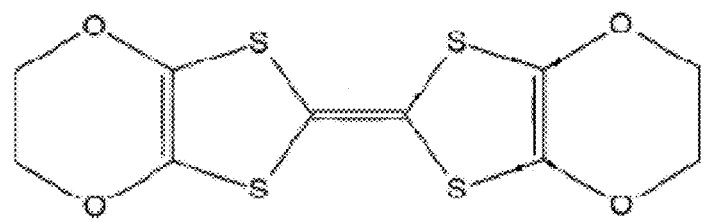
FIG. 3: Structure of BEDO-TTF.

Conductive polymer complexes of the illustrative embodiment are prepared by doping optical polymers (e.g. bisphenol A polycarbonate (PC), poly(methyl methacrylate) (PMMA) or polystyrene (PS)) with bis(ethylenedioxy)-tetrathiafulvalene (BEDO-TTF) (see FIG. 3). BEDO-TTF is known to form conductive complexes with a variety of organic acceptors and various anions. About 100 charge transfer complexes have been synthesized using BEDO-TTF as a donor molecule but only 64 species have shown metallic characteristics. Key studies have been conducted on BEDT-TTF charge transfer complexes. Previous work has shown that BEDO-TTF is a candidate for the preparation of crystalline organic metals, superconductors and metal-like composites BEDOTTF appears as tiny, orange crystals with sub millimeter dimensions and exists as an important organic $\pi$-donor. Its tendency to self-aggregate results in the formation of structurally and electronically two-dimensional organic layers. Surface conductive films are produced when the dyed polymer is exposed to iodine or bromine via a two step reticulate doping method described below.

CCO Biding

Another aspect of the invention includes the use of conjugated conductive oligomers (CCOs). Specific targets include surface-selective molecules that bind to metal surfaces creating assemblies of molecular sensors with optimized surface selectivity. For example, Bazan et al. has pioneered the synthesis of water-soluble, light harvesting conjugated polymers and their use in the optical amplification of fluorescent biosensors, both in solution and in the solid state. With the advent of conducting organic materials, new challenges have arisen that must be overcome to enable full use of the potential applications and benefits offered by these materials. To make good contact between metal electrodes and conducting molecules, one must covalently bind the conjugated molecules to the surface or use a suitable self-assembled monolayer (SAM) that improves adhesion. This problem is addressed by taking advantage of novel synthetic methods for preparing CCOs with thiol groups in conjugation with the delocalized $\pi$ framework for modification of gold electrodes. Changes in the surface properties can be detected, inter alia via surface forces based techniques.

The recently reported selective cleavage of arylmethyl thioethers to S-acetyl groups developed from Bazan provides a convenient protocol for the synthesis of optoelectronic molecules with gold-specific functionalities. Since the arylmethyl thioether is tolerant of many chemical reaction conditions, it is possible to elaborate molecular design to incorporate fragments that modulate the barrier of injection into the charge transporting conjugated polymer layer. Typical examples of the molecules already prepared by this method are shown in FIG. 4.

Figure 4:
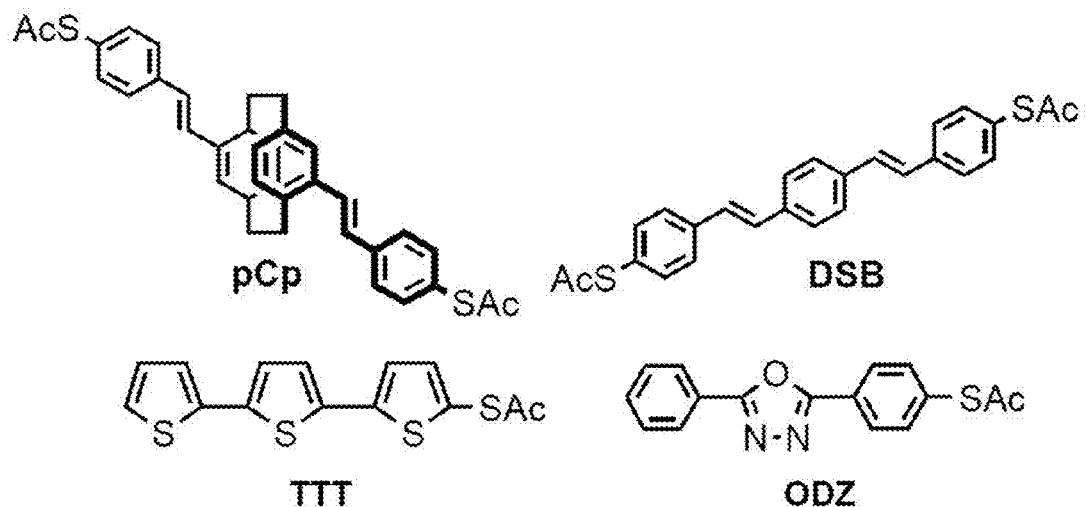
FIG. 4: Selective cleavage methodology.
Figure 5:
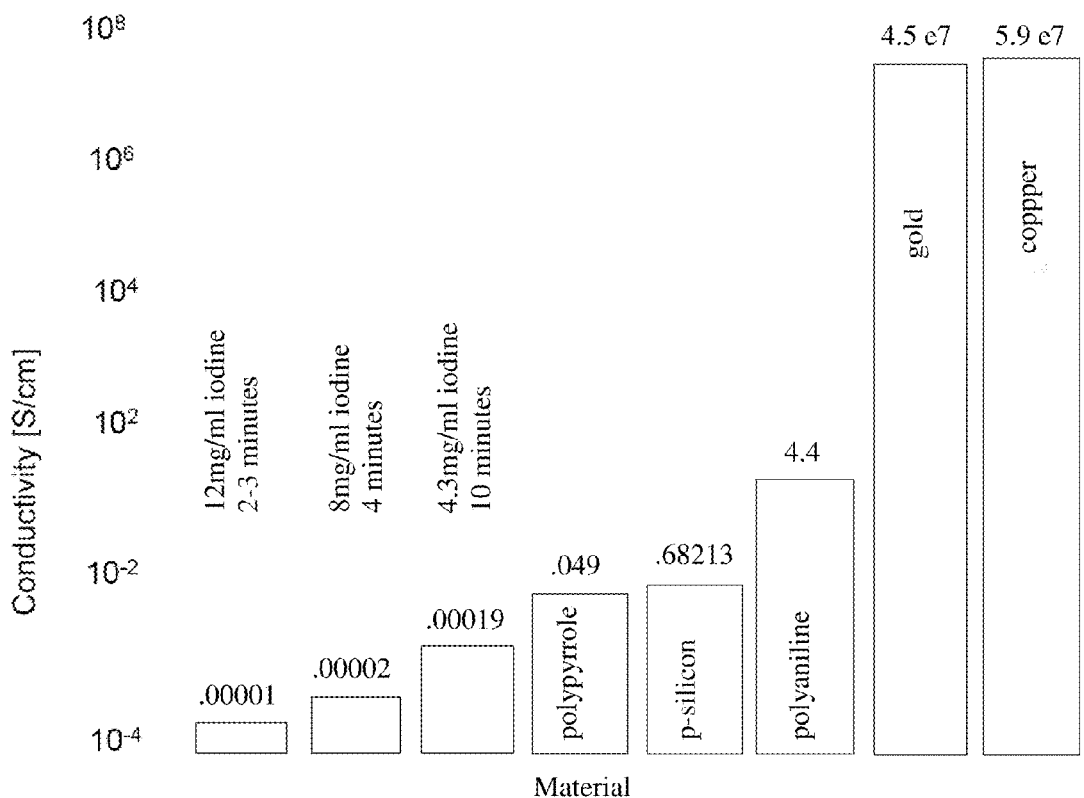
FIG. 5: Conductivity measurements comparison between common conducting materials and BEDO/PC/12 films prepared at different conditions.

Referring now to FIG. 4; compounds pCp and DSB were recently used to examine the tunneling current across a single monolayer and to probe for the first time the effect of through-space delocalized states. Compounds TTT and ODZ were shown to decrease substantially the operating voltages of FETs and LEDs by providing a monolayer-functionalized gold electrode (FIG. 5). Comparison of TTT and ODZ yields information about how the dipole at the surface influences charge injection. We will maintain constant communication with Dr. Gui Bazan at UCSB who will assist us in the synthesis of the CCOs.

Film Assembly—Two Step Reticule Method

Previous work using PC and the two step reticule method included a first step comprised of preparation of non-conductive PC films doped with 2% (w/w) BEDOTTF film. The dye and polymer, 5% (w/w) were dissolved in methylene chloride and poured into a mold with an optical surface. The solvent was slowly evaporated via a pin-hole cover and the film released from the mold. In the second step, the film was exposed to a mixed vapor of iodine and methylene chloride. The concentration of iodine and the exposure time were varied to minimize resistivity. Data comparing common conducting materials to BEDO/PC/Iodine films are shown in FIG. 5. The data in FIG. 5 shows that the film conductivity is high if the concentration of I2 solutions is low. Consequently, the films need to be exposed to I2 for longer periods of time.

Here, the previous reticule method is modified. Modifications to the method include expansion to include bromine, another halogen. In addition, a variety of different solvents are used with the halogens, since the proper selection of solvent and evaporation technique influence surface conductivity. Solvents are selected based on initial screening to ensure solubility of the dye and polymer. The invention is the first to develop and use the electric field enhanced crystallization of the dye-halogen complex. In a preferred embodiment, the halogen solutions are delivered to the surface of the film via an induction based fluidic device that flies fluids in an electric field. It is also possible to alter the procedure and expose the films to an electric field when they are simultaneously exposed to the halogen-solvent vapor.

Film Assembly—Gold Nanoparticle Layer

Figure 6:
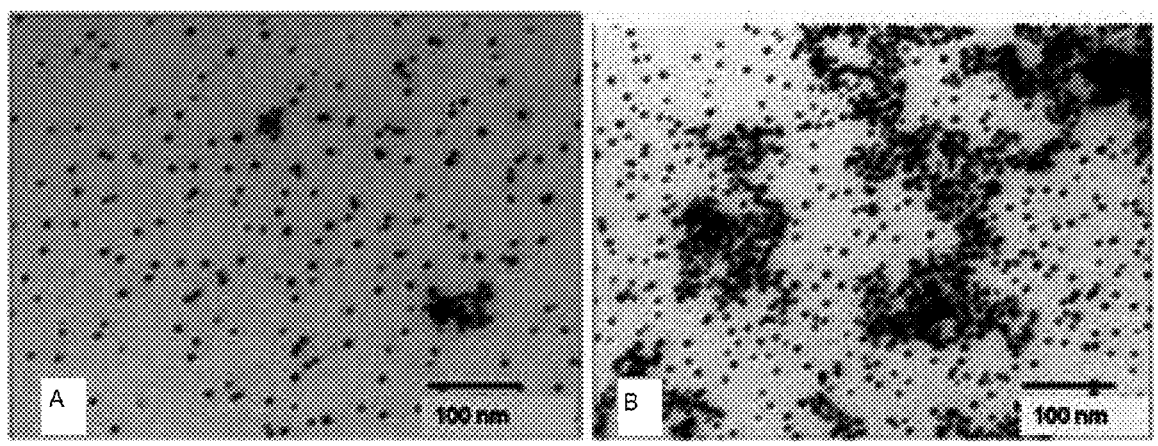
FIG. 6: TEM images of gold particles deposited by A) IBF, B) Micropipette.

Gold nanoparticle (5 to 50 nm) are applied to the surface of the film via spin coating creating an organic/inorganic hybrid film. Water was used as the solvent to suspend the nanoparticles. The nanoparticle solutions an be deposited on the film surface via induction based fluidics. FIG. 6 shows a sample of gold nanoparticle deposition on a film via IBF. A sample was micropipetted on the surface for comparison. The IBF technique allows for controlled dispersion and the density of the gold particles can be varied by altering the concentration.

Detection of IED Motifs Using CCOs

Figure 7:
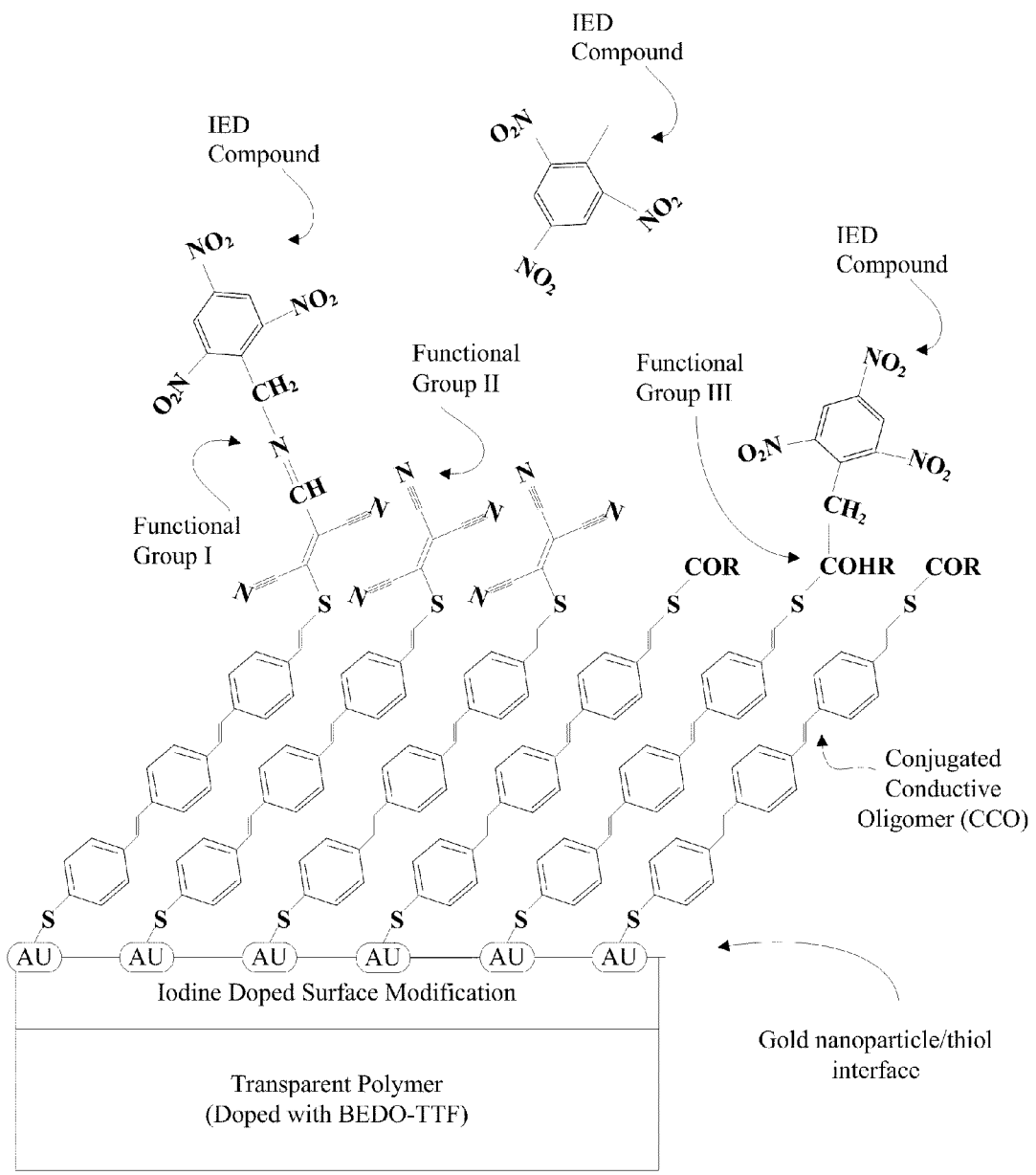
FIG. 7: Schematic representation of the TCC/Au/CCO assembly and IED compound recognition.
Figure 8:
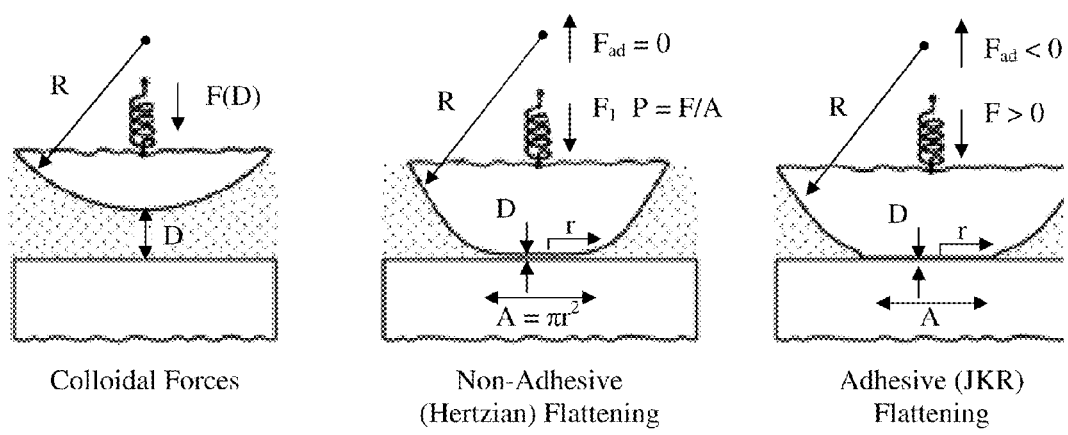
FIG. 8: (left) Schematic of the SFA, showing the parameters that can be directly measured and the surface profiles that can be monitored by MBI. For 'nonadhering' surfaces the adhesion force is zero, Fad=0, and the shape of the flattened surfaces under a given load F is given by the 'Hertz theory' (center). For 'adhering' surfaces Fad is finite, and the shape of flattened surfaces is given by the 'Johnson-Kendall-Roberts' (JKR) theory (right).

In organic/inorganic hybrids, the gate dielectric-organic contact influences the current flow between source and drain by perturbing the morphology, and therefore the bulk charge mobility of the semi-conducting material. Most organic charge transport materials do not wet polymeric/Au surfaces due to a difference in polarity. Molecules therefore tend to cluster into islands and do not form uniform thin films. The invention overcomes the problems of the prior art by taking advantage of novel synthetic methods for preparing oligomers with thiol groups in conjugation with the delocalized $\pi$ framework for modification of the polymer/Au/CCO interface (FIG. 5). The reaction between Au nanoparticles and the thiol end-terminal in the CCOs occurs with high affinity. This binding event is robust and produces a homogenous layer with high surface density (FIG. 7).

The detection portion is achieved with the advent of functionalized CCO materials decorating the surface of the TCCs. Several functional groups are known to attach IED compounds with high selectivity. Two examples of such functional groups are depicted in FIG. 7. Since nitroaromatics do bind with electron rich a-conjugated systems, they dramatically change the optoelectronic properties of the film underneath recording an unambiguous signal.

Figure 2:
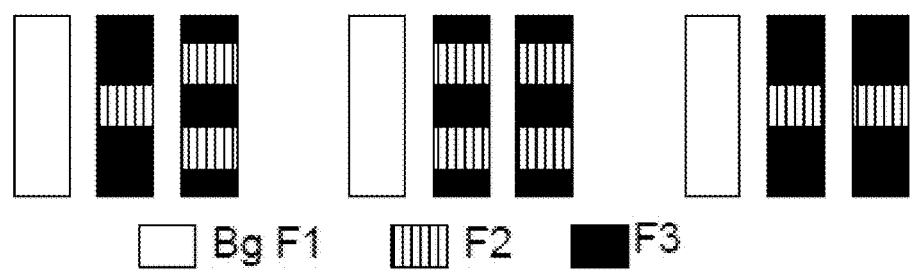
FIG. 2: Schematic representation of a simple 3BSys array. The region in gray will contain a generic functional group providing a background signal (Bg F1). A combination of patterns with two other functional groups, Bg F1 F2 F3 F2 and F3, will provide significantly different signals.

The subtle change in conductivity by each functional group is recorded by the design simple arrays of TCCs by using conventional microfabrication techniques and using a 3BSys as depicted in FIG. 2. One of the advantage of having arrays of three and controlled areas decorated with different functional groups is that the presence of secondary high explosives (i.e., TNT, RDX, PETN) can be detected even though the vapor pressure of some of these chemicals is relatively low.

Detection of IED Using Hyphenated Surface Analysis Techniques

Physical and chemical changes of the structures and interfaces at the nanoscale inherently affect the performance of the overall material and its interface. The detection and monitoring of such changes as well as order and process large and sustainable TCCs assemblies simultaneously is possible if different surface characterization techniques are used together. Past research on measuring surface forces, (e.g., of dielectrics, polymer coatings, Clays, and metal surfaces) and plasma assisted polymer grafting on dielectric films demonstrated the strength of in situ real time Attenuated Total Reflection Fourier Transform Infrared (ATR-FTIR) spectroscopy and the Surface Forces Apparatus (SFA) technique. These techniques offer an effective means of probing interfacial phenomena and intermolecular forces on thin films and their surroundings, as well as in-situ processing by applying pressure, rolling and shear.

Therefore, another aspect of the invention includes the integration of the Surface Forces Apparatus (SFA) technique with Infrared (IR) spectroscopy (IR-SFA) in order to investigate static and dynamic surface interactions in a well-defined contact geometry and to determine chemical state between the surfaces and interfaces simultaneously. It has been noted that simple materials in restricted geometries, such as pores or cracks, exhibit extraordinary properties. Some of these properties include effective viscosity, the diffusion coefficient and the melting point. This new technique is able to investigate molecular confinement, provide by the crossed-cylinder configuration encountered in the SFA experiments, related to chemical bonding and reactions. This is a task that no other currently existing technique can accomplish.

Surface Forces Apparatus (SFA): The SFA quantitatively measures intermolecular forces, both attractive and repulsive, between two layers supported on solid or soft substrates as a function of distance or surface separation. The surfaces are brought into contact or separated in a highly controlled fashion by using micrometers and piezoelectric displacement transducers. The forces are measured from the deflection of a spring supporting one of the surfaces using Hooke's law (FIGS. 9A and 9B).

Figure 9A:
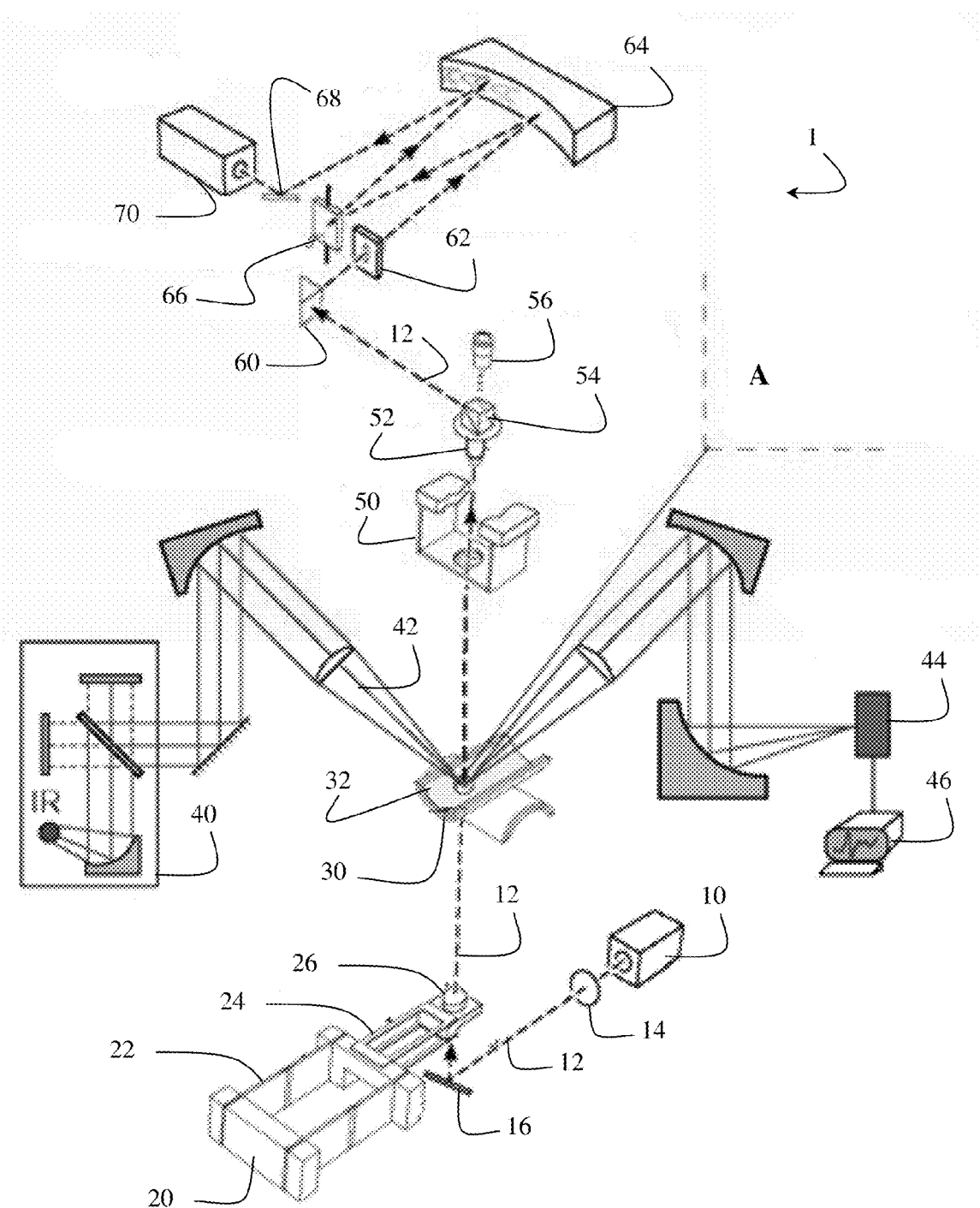
FIGS. 9A and 9B.
Figure 9B:
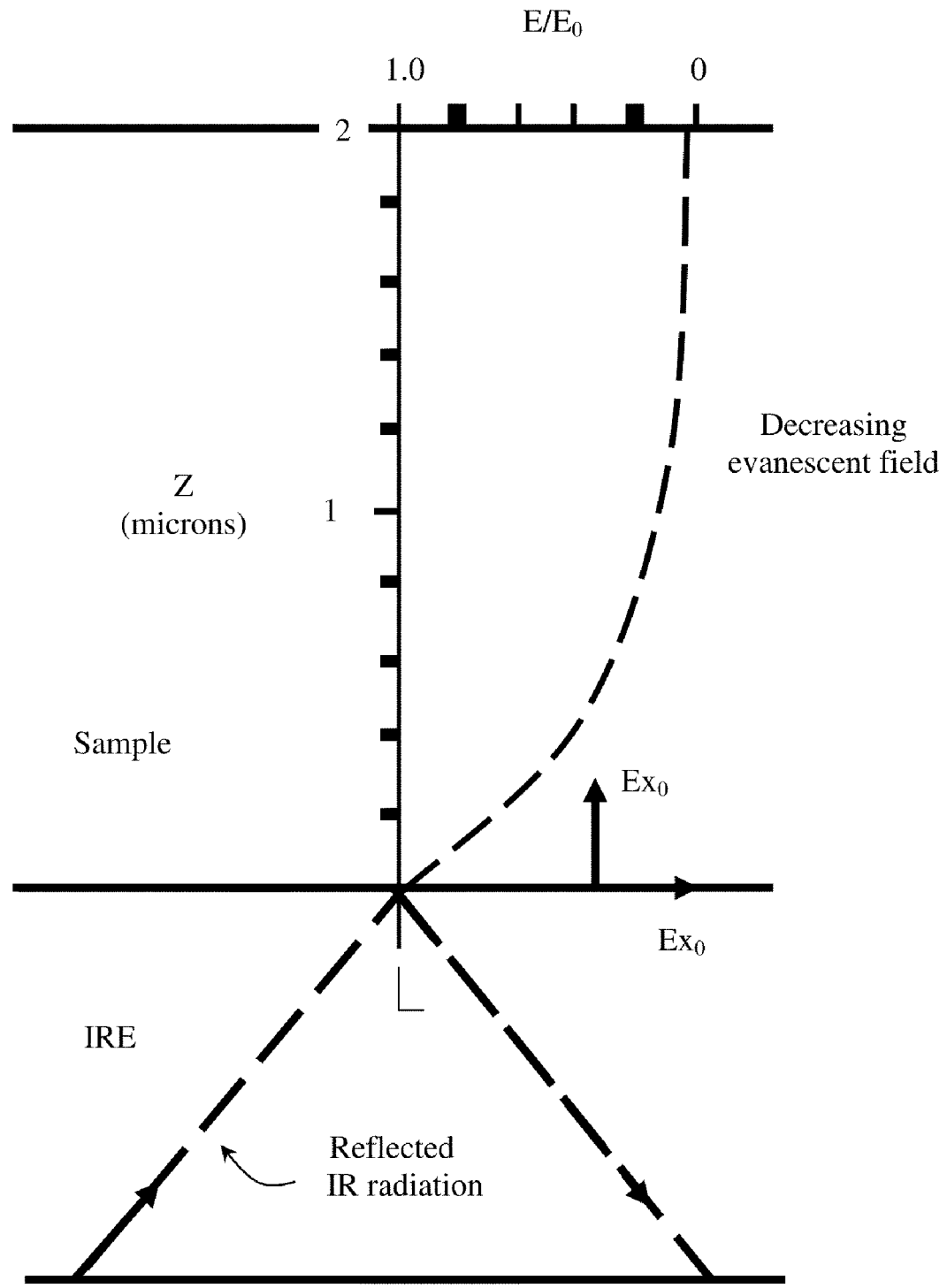

An illustrative IR-SFA device is shown in FIG. 9A. Generally; IR-SFA device (shown generally as element 1) includes white light source 10 for generating light path 12 which initially passes through collimating lense(s) 14. Light path 12 is then diverted by mirror 16 toward bimorph slider 20. Bimorph slider 20 further includes piezoelectric strips 22, cantilevering spring 24 and crossed silica discs 26. Light path 12 then passes through a series of thin (i.e. 55 nm) silver layers 30 and curved mica sheets 32.

Light path 12 continues past silver layers 30 and curved mica sheets 32 to friction detecting device 50. Friction detecting device 50 further includes microscope objective 52, prism 54 and viewing port eyepiece 56. Prism 54 redirects light path 12 toward prism 60, which in turn redirects light path 12 through spectrometer slit 62 onto concave mirror 64. Concave mirror 64 redirects light path 12 on diffraction grating 66, which returns light path 12 to concave mirror 64. Light path 12 is redirected from concave mirror 64 a second time toward mirror 68 which redirects light path 12 to video camera 70.

In addition to white light source 10, IR-SFA system 1 also includes IR source 40. IR source 40 generates IR path 42 which is redirected by a series of IR reflective surfaces onto silver layers 30 and mica sheets 32. IR path 42 is then redirected by a second series of IR reflective surfaces and is ultimately monitored by DTGS detector 42 and data acquisition device 44. Detail A is shown in FIG. 9b showing the decreasing evanescent field and reflected IR radiation from the IR source.

The SFA technique is conceptually similar to the AFM or any other mechanical force-measuring technique that employs a cantilever spring to measure forces, and a series of springs and piezoelectric crystals to control surface separations. In addition, because the surfaces are macroscopic (local radius R~1 cm and contact diameters 2r, 5-500 μm) an optical technique using multiple beam interference fringes (known as Fringes of Equal Chromatic Order or FECO) can be used to accurately and unambiguously measure the absolute (rather than relative) surface separation D to 1 Å or better as well as the mean refractive index n of the liquid or solid film (of thickness D) between the surfaces. By recording the changing FECO fringe pattern with time, any changes in these parameters can be visualized and monitored in real time at the Å level, thereby providing direct information on such phenomena as metal oxide dissolution, membrane deformation, layer fusion, friction behavior, changes in film thickness, refractive index and shape. The SFA can measure very weak forces (nN) with 1 Å resolution and is capable of mapping out the full interaction potential between the two surfaces, i.e., the force-distance curves. The shearing and/or rolling between two surfaces is done via friction sensing device 50 or 'shearing attachment' employing bimorph slider 20.

Attenuated total reflection Fourier transform infrared (ATR-FTIR) spectroscopy: ATR-FTIR spectroscopy has been used as a surface diagnostic for the last three decades. Here, each reflection on the optically denser IR transparent substrates (i.e., BaF2) that mimic the cross-cylinder configuration in the SFA adds to the IR absorbance, which results in sub-monolayer detection sensitivity of surface adsorbates.

The Infrared-Surface Forces Apparatus (IR-SFA): The modification of the SFA and the coupling of these instruments is shown in FIGS. 9A and 9B. This new instrument, IR-SFA, simultaneously uses three independent powerful surface characterization techniques, the SFA, Fourier transform infrared (FTIR) spectroscopy, and MBI. Thus, this research facilitates the development of an ancillary, generic, and quantitative technique for identifying and classifying variations in crystalline structures, functionalized polymeric films, conducting layers, and their interactions.

The IR spectral resolution makes it possible to resolve molecular stretches. Thus, structure determination and the time resolution (~1 s) is compatible with kinetics taking place as load or composition are varied. It is also possible calibrate the movement of the upper surface device with respect to the angle adjusting mirrors of the IR beam entering the SFA. The penetration depth (dp=0.3λ, for BaF2/air at 45°) of the IR beam have been computed following the theory of Buffeteau et al.

Figure 10:
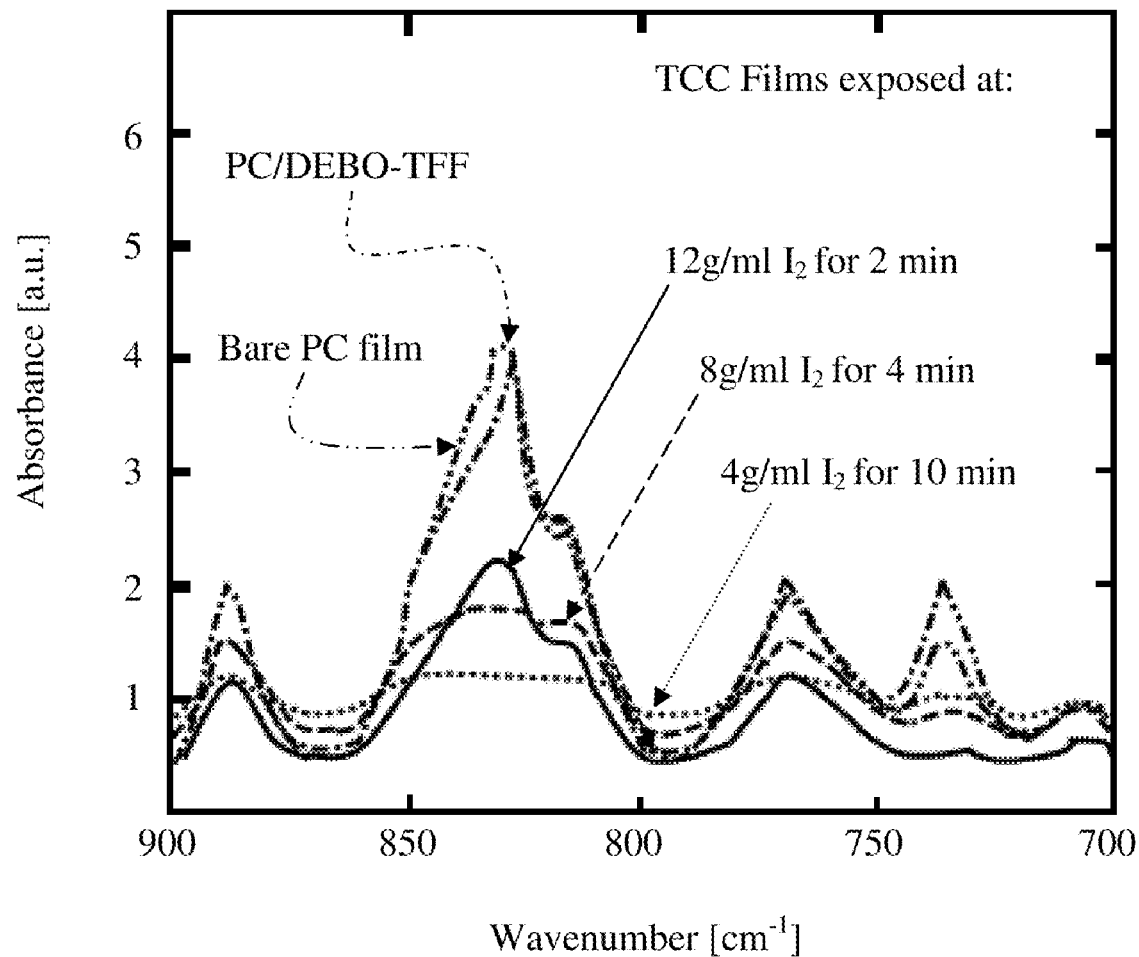
FIG. 10: ATR-FTIR spectra collected for bare PC, dye doped PC (BEDO-TTF/PC), and I2 modified films. Images of the film structures where taken with an optical microscope.

One could employ this technique to differentiate the adsorbates' optical (using MBI), chemical, and mechanical responses of the TCCs that have reacted with an IED compound from those on the film that are intact. Studies with ATR-FTIR on films exposed to different conditions of doping I2 (same films as shown in FIG. 5) show significant differences with respect to the spectra for bare PC and BEDO-TTF/PC in the peaks specific to C-Halogen binding (not shown) and in the peaks designated to para-substitution (FIG. 10). The structure of the films also changes significantly. The bare PC and BEDOTTF/PC films are homogenous at this scale (scale bar corresponds to 20 µm), where as the films that have been exposed to I2 show an intricate maze-like structure (FIG. 10).

Optical Properties: UV/Visible Spectroscopy and Confocal Microscopy

UV/Visible spectroscopy can be used to monitor the optical transparency and dye stability. It is well known that halogen vapor treatment induced changes in the optical properties. The pink, dyed films become different colors ranging from green to purple depending on the treatment. Optical absorptions will be related to conductivity in an attempt to optimize electrical properties. A laser scanning confocal microscope can be used to record 3D images of the reticulate processed films. This reveals the crystal morphology versus depth. All of this can be used to identify structures that exhibit optimum conductivity and in addition to the MBI technique included in the SFA measurements.

Electrical Properties: Surface Conductivity; Dielectric Analysis (DEA)

Background studies were conducted measuring resistivity on the films via a four-point probe (FIG. 6). The probe consisted of four linearly arranged and equally spaced electrodes, which remain in contact with the sample. Current (I) is supplied to the material through two outside probes using a Keithley 6221. DC and AC current source, and voltage (V) across the other two inside probes, was determined by Keithley 6514 system electrometer. Resistivity of doped composite films was measured randomly at different locations on film surfaces using the four point probe. Eight repeated measurements were carried out and the average value of the measured resistivities for each film was reported. Voltages were measured in volts and current in milliampere. Electrical conductivity, σ, was obtained by simply inverting the corresponding values of the resistivity. Table summarizes initial results:

TABLE 1

Surface resistivity and conductivity of iodine treated composite films

| BEDO-TTF (wt %) in PC | Iodine conc. in DCM (g L$^{-1}$) | Exposure time (mins) | Surface Resistivity (KΩ/□) | Conductivity (S Cm$^{-1}$) |
|---|---|---|---|---|
| 2 | 12 | 2 | 88.516 | 1.142E-05 |
| 2 | 8 | 4 | 45.549 | 2.288E-05 |
| 2 | 4.3 | 10 | 5.440 | 1.881E-04 |

Dielectric analysis can be used to monitor dye-polymer interactions. Dielectric analysis can be performed, for example, using a TA Instruments DEA 2970. Measurements are recorded in 5° C. increments from −150 to 270° C. at frequencies from 0.3 Hz to 100 KHz. In dielectric analysis (DEA) the material is exposed to an alternating electric field generated by an applied sinusoidal voltage. The applied electric field causes the alignment or induction of dipoles in the material which results in polarization. Both the polymers and the dye can possess permanent dipole moments. DEA measures two fundamental characteristics of the composite, capacitance and conductance as a function of temperature and frequency. The capacitive nature of the material is its ability to store electrical charge while the conductive nature is the materials ability to transfer electric charge. One feature of DEA is that this spectroscopy allows for investigation of molecular mobility, or relaxations of the material. The complex permittivity, ∈*, of a system is defined:

$$\epsilon^* = \epsilon' - i\epsilon''$$

Where ∈' is the real part of the complex relative permittivity (dielectric constant) and represents the amount of dipole alignment both induced and permanent. ∈" is the dielectric loss (loss factor) and represents the dipole loss factor plus ionic conduction. At high temperatures the ionic conductivity can be measured from:

$$\varepsilon''_{ion} = \frac{\sigma_{AC}}{\omega \varepsilon_o}$$

Plots of conductivity versus frequency can be extrapolated to zero to yield DC conductivity. The activation energy for conductivity is calculated from the slope of plots of ln (conductivity) versus 1/T. The porphyrin dye (not conductive in this case) decreased the activation energy for ionic conductivity by 13 kcal/mol as compared to the PMMA control.

From this type of information a picture of the effect of dye and matrix on molecular mobility emerges. The dye plasticizes the polymer matrix and enhances ionic conduction.

For large-area of chemically active surfaces, integration of mechanical, chemical, and electrical effects on device fabrication becomes complex and requires proper control over the entire process sequence. Synthetic methodologies must be extended from the molecular level up to, and from the macroscopic level down to, the nanoscale to aid in the development of new integrated materials with enhanced physical properties and functionality. The ordered arrays of conjugated polymeric and oligomeric materials, when well-aligned, become excellent semi-conductors that can be used in new types of optical and electronic sensors because alignment induces high charge mobility, chemical affinity and optical control.

Figure 11:
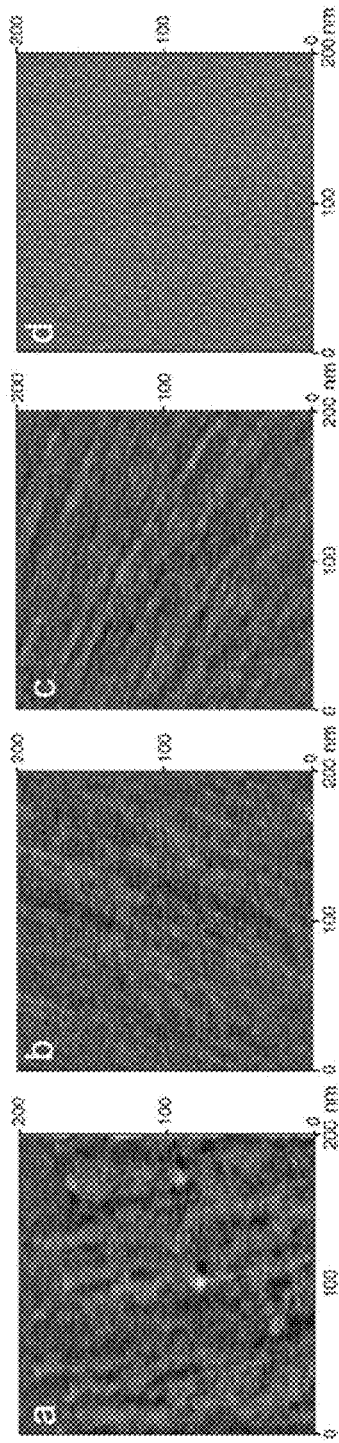
FIG. 11: AFM phase scans of confined organic films after shearing a) in vertical direction at V=5.6 μm/s before freezing in LN2, b) in the vertical direction at V=55.6 μm/s before freezing in LN2 and c) in the horizontal direction at the same conditions as b. d) AFM micrograph of confined but unsheared film. Higher shearing velocity generated thinner and longer linear bundles of the material.

FIG. 11 shows four AFM phase images of confined hydrocarbon (n-eicosane) films. The films were confined and processed in a Surface Forces Apparatus (SFA) between two molecularly smooth mica surfaces using a shearing device and then frozen with liquid N2 to preserve surface organization. Three images show the materials' interface after being subjected to shear alignment (FIGS. 11a-13c). It was possible to obtain images of the structures of the films during steady-state sliding, revealing striped domains °2 Å in height and a few nanometers in width. The surface structure depends on the mechanical processing conditions such as pressure of confinement, shearing direction, sliding velocity and sliding distance, as well as time. On the other hand, confined but unsheared films yielded completely featureless images (FIG. 11d). These results are the first direct experimental shear-induced ordering in nano-confined films resulting in layering and domain formation. Consequently, it is possible to render effective control of the surface morphology.

Figure 12:
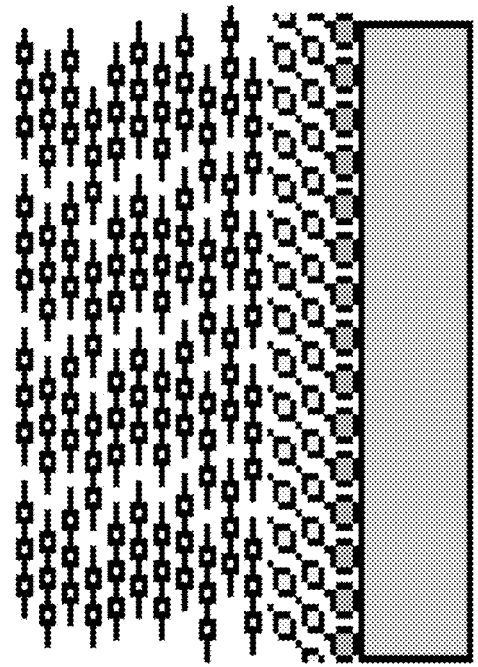
FIG. 12: Shear alignment. Order can be created by shearing. Additional alignment can be induced by having monolayers or surface chemical groups which can alter the surface alignment of films.

As noted earlier, the SFA technique can be used to determine the interactions between interchains of CCOs and with respect to the substrate interface (TCCs). These interactions can be measured before and after processing and under various processing conditions (solvent type, pressure, shear, etc). Orientation, shape and position of the TCC/CCO materials are sensitive to the intrinsic alignment, stress, and the structure of the surface underneath. For a material that has no definite structure in the bulk, a nano-structured substrate can order the first few molecular layers only, after which the bulk 'structure', which is random in our case, takes over. Order or alignment is lost within a few layers of the substrate in fluid structures. On the other hand, if the disordered films are aided in the processing. FIG. 12 shows molecular alignment with respect to shear stresses on the films. For the case of mechanical ordering, the composite material takes on a bulk structure right from the first layer when press against the substrate (known as 'planar' alignment).

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A transparent conductive composite comprising:
a polymer composite matrix having a halogen-doped surface;
a conductive nanostructure disposed in the polymer composite matrix;
a conjugated conductive oligomer having a first end and a second end, the first end of the oligomer being connected to the conductive nanostructure disposed in the upper surface of the polymer composite matrix; and
a functional group having a first end covalently bound to the second end of the conjugated conductive oligomer, and a second end selected to bind a predetermined target.

2. The transparent conductive composite of claim 1, wherein the polymer composite matrix comprises an optical polymer.

3. The transparent conductive composite of claim 2, wherein the optical polymer is doped with bis(ethylenedioxy)-tetrathiafulvalene.

4. The transparent conductive composite of claim 2, wherein the optical polymer is selected from the group consisting of bisphenol A polycarbonate, poly(methyl methacrylate), or polystyrene.

5. The transparent conductive composite of claim 1, wherein the polymer composite matrix is doped with a halogen selected from the group consisting of iodine and bromine.

6. The transparent conductive composite of claim 1, wherein the conductive nanostructure is gold.

7. The transparent conductive composite of claim 1, wherein the conductive nanostructure is 5 to 50 nm.

8. The transparent conductive composite of claim 1, wherein the first end of the conjugated conductive oligomer is thiolated.

9. The transparent conductive composite of claim 1, wherein the predetermined target is a constituent of an improvised explosive device selected from the group consisting of nitroamine, nitroaromatic, and nitrate ester compounds.

10. The transparent conductive composite of claim 1, wherein the functional group is a nitro-derivative receptor.

11. The transparent conductive composite of claim 10, wherein the functional group is selected from the group consisting of

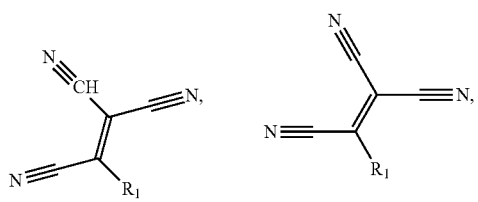

$COR_1$ and $COHR_1$,
wherein $R_1$ is S.